United States Patent
Gu et al.

(10) Patent No.: US 10,490,852 B2
(45) Date of Patent: Nov. 26, 2019

(54) ADDITIVE FOR ELECTROCHEMICAL ELEMENT, ELECTROLYTE COMPRISING SAME, ELECTRODE, AND ELECTROCHEMICAL ELEMENT

(71) Applicant: LG Chem, Ltd., Seoul (KR)

(72) Inventors: Minji Gu, Daejeon (KR); Jeong Hwan Koh, Daejeon (KR); Soojung Yeo, Daejeon (KR); Myung Jin Chun, Daejeon (KR)

(73) Assignee: LG Chem, Ltd. (KR)

( * ) Notice: Subject to any disclaimer, the term of this patent is extended or adjusted under 35 U.S.C. 154(b) by 214 days.

(21) Appl. No.: 15/317,576

(22) PCT Filed: Apr. 24, 2015

(86) PCT No.: PCT/KR2015/004104
§ 371 (c)(1),
(2) Date: Dec. 9, 2016

(87) PCT Pub. No.: WO2015/199328
PCT Pub. Date: Dec. 30, 2015

(65) Prior Publication Data
US 2017/0162904 A1    Jun. 8, 2017

(30) Foreign Application Priority Data

Jun. 27, 2014  (KR) .................. 10-2014-0080200

(51) Int. Cl.
*H01M 10/0567* (2010.01)
*H01M 10/052* (2010.01)
*C07F 7/18* (2006.01)

(52) U.S. Cl.
CPC ....... *H01M 10/0567* (2013.01); *C07F 7/1804* (2013.01); *H01M 10/052* (2013.01); *H01M 2300/0025* (2013.01)

(58) Field of Classification Search
CPC ........... H01M 10/0567; H01M 10/052; H01M 2300/0025; C07F 7/1804
USPC ...................................................... 429/498
See application file for complete search history.

(56) References Cited

U.S. PATENT DOCUMENTS

| | | | |
|---|---|---|---|
| 4,331,802 A | 5/1982 | Wiesner et al. | |
| 6,872,493 B2 | 3/2005 | Yamada et al. | |
| 2002/0076619 A1* | 6/2002 | Yamada | H01M 10/052 429/324 |
| 2009/0280414 A1* | 11/2009 | Koh | H01M 4/13 429/304 |
| 2011/0217599 A1* | 9/2011 | Yamamoto | H01M 2/16 429/306 |
| 2012/0034532 A1 | 2/2012 | Kim et al. | |
| 2012/0205595 A1 | 8/2012 | Schulz-Dobrick et al. | |
| 2012/0298193 A1 | 11/2012 | Ihn et al. | |

FOREIGN PATENT DOCUMENTS

| | | |
|---|---|---|
| CN | 1807431 A | 7/2006 |
| CN | 101517813 A | 8/2009 |
| CN | 102265446 A | 11/2011 |
| CN | 101931107 B | 10/2012 |
| CN | 102796246 A | 11/2012 |
| DE | 1182232 B | 11/1964 |
| EP | 1202373 A2 | 5/2002 |
| EP | 2851989 A1 | 3/2015 |
| JP | H01233288 A | 9/1989 |
| JP | H05202077 A | 8/1993 |
| JP | 2002134169 A | 5/2002 |
| JP | 3497812 B2 | 2/2004 |
| JP | 2004307655 A | 11/2004 |
| JP | 2009295397 A | 12/2009 |
| JP | 2010103052 A | 5/2010 |
| JP | 2011134705 A | 7/2011 |
| KR | 20120079395 A | 7/2012 |
| TW | 201238131 A | 9/2012 |
| WO | 2013187380 A1 | 12/2013 |

OTHER PUBLICATIONS

S. Gharaati et al: "Highly efficient and selective trimethyl silylation of alcohols and phenols w/ hexamethyldisilazane catalyzed by polystyrene-bound tin(IV)porphyrin", Polyhedron, vol. 35, No. 1, Jan. 20, 2012 (Year: 2012).*
Supplementary European Search Report for Application No. EP 15812838, dated Nov. 10, 2017.
Gharaati, et al., "Highly efficient and selective trimethylsilylation of alcohols and phenols with hexamethyldisilazane catalyzed by polystyrene-bound tin(IV) porphyrin", Polyhedron, Jan. 20, 2012, pp. 87-95, vol. 35, No. 1.
Henglein, et al., "Über Reaktionen von natürlichen Gerbstoffen und deren Bausteinen mit Trimethylchlorsilan", Chemische Berichte, Jan. 1, 1959, pp. 2585-2592, vol. 92, No. 7 (Machine-generated English translation is attached).
Faleschini, et al., "29Si -und 13C-NMR-Untersuchungen zur Struktur persilylierter Urazole", Monatshefte Für Chemie—Chemical Monthly, Apr. 1, 1988, pp. 457-461, vol. 119, No. 4 (Machine-generated English translation is attached).
International Search Report from PCT/KR2015/004104, dated Jul. 15, 2015.
Delomenède, et al., "Development of Novel Antiatherogenic Biaryls: Design Synthesis, and Reactivity." J. Med. Chem., 2008, vol. 51, pp. 3171-3181.
Phillips, et al., "Spectral Techniques for Structural Analysis of the Cotton Terpenoid Aldehydes Gossypol and Gossypolone." J. Agric. Food Chem., 1990, vol. 38, pp. 525-528.

(Continued)

*Primary Examiner* — Gary D Harris
(74) *Attorney, Agent, or Firm* — Lerner, David, Littenberg, Krumholz & Mentlik, LLP

(57) ABSTRACT

The present specification relates to an additive for an electrochemical device including a compound having a silyloxy group, and an electrolyte, an electrode and an electrochemical device.

14 Claims, No Drawings

(56) References Cited

OTHER PUBLICATIONS

El-Gamel, et al., "Synthesis, spectroscopic characterization, and X-ray crystal structure of tiris(trimethylsilyl)cyanurate." Journal of Coordination Chemistry, vol. 62, No. 8, Apr. 20, 2009, pp. 1278-1284.
Kasano, et al., "A facile [4+1} type synthetic route to thiophenes from dienol silyl ethers and elemental sulfur." Tetrahedron 62, Oct. 13, 2005, pp. 537-542.
IPO Search Report from Taiwan Patent Application No. 104113275, dated Mar. 11, 2016.
Chinese Search Report for Application No. 201580032288.3 dated Aug. 6, 2018.

\* cited by examiner

ADDITIVE FOR ELECTROCHEMICAL ELEMENT, ELECTROLYTE COMPRISING SAME, ELECTRODE, AND ELECTROCHEMICAL ELEMENT

CROSS-REFERENCE TO RELATED APPLICATIONS

The present application is a national phase entry under 35 U.S.C. § 371 of International Application No. PCT/KR2015/004104, filed Apr. 24, 2015, published in Korean, which claims priority to and the benefits of Korean Patent Application No. 10-2014-0080200, filed with the Korean Intellectual Property Office on Jun. 27, 2014, the entire contents of which are incorporated herein by reference.

TECHNICAL FIELD

The present specification relates to an additive for an electrochemical device. In addition, the present specification relates to an electrolyte and an electrode including an additive for an electrochemical device. Furthermore, the present specification relates to an electrochemical device including an additive for an electrochemical device.

BACKGROUND ART

Lithium secondary batteries have grown in their importance and use as medium and large sized power supply units of electric vehicles, hybrid-type vehicles, mass power storage devices and the like, and power supply units of mobile devices. Recently, current density and voltage increases of batteries have been continuously pursued through the development of electrode active materials in a lithium secondary battery field, and overall performance enhancement of materials used has been required reflecting such performance enhancement. Securing a property of cycle capacity retention according to capacity and voltage increases in such lithium secondary batteries is one of the properties essentially required for battery performance enhancement. Stabilization of an electrode active material, which is one method of securing such a property, is largely related to capacity retention, and stabilization of an anode active material including a transition metal may perform an important role in retaining cycles, and is considered to be directly related to capacity retention under a high voltage and high temperature condition. Development of various materials for improving various performances such as capacity, a lifespan and a high temperature property of lithium secondary batteries have been required.

DISCLOSURE

Technical Problem

The present specification provides an additive for an electrochemical device, and an electrolyte, an electrode and an electrochemical device including the additive.

Technical Solution

One embodiment of the present specification provides an additive for an electrochemical device including a compound represented by the following Chemical Formula 1.

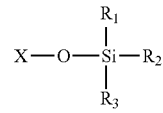

[Chemical Formula 1]

In Chemical Formula 1,

X is a substituted or unsubstituted monovalent aryl group, or a substituted or unsubstituted monovalent heteroaryl group, and $R_1$ to $R_3$ are the same as or different from each other, and each independently hydrogen or a monovalent organic group.

Another embodiment of the present specification provides an electrolyte including the additive for an electrochemical device.

Still another embodiment of the present specification provides an electrode provided with a membrane formed by an oxidative polymerization reaction of a material produced by the compound of Chemical Formula 1 collecting an acid component on a portion or the whole of a surface.

In addition, one embodiment of the present specification provides an electrochemical device including an anode, a cathode, a separation membrane and an electrolyte, wherein the electrolyte includes the additive for an electrochemical device, and/or a membrane formed by an oxidative polymerization reaction of a material produced by the compound of Chemical Formula 1 collecting an acid component is provided on a portion or the whole of a surface of at least one of the anode and the cathode.

Advantageous Effects

An additive for an electrochemical device according to embodiments of the present specification neutralizes an acid component such as HF in an electrolyte of an electrochemical device, and therefore, can minimize electrode surface damage due to an electrolyte decomposition reaction with the acid component on the electrode surface. In addition, an additive for an electrochemical device according to embodiments of the present specification forms an effective protective membrane on an electrode surface by an oxidative polymerization reaction after collecting an acid component such as HF, and has a function of preventing further decomposition of an electrolyte, and protecting the electrode from an attack of lithium salt decomposition products. In other words, an additive for an electrochemical device according to embodiments of the present specification is a multifunctional additive capable of preventing battery performance decline caused by an acid component by collecting the acid component such as HF, particularly improving a high-temperature cycle property, enhancing high-temperature storage efficiency by reducing a voltage drop during the high-temperature storage, and simultaneously improving various properties such as capacity, a lifespan, an output and a high-temperature property of a secondary battery through forming a protective membrane on an electrode surface.

MODE FOR DISCLOSURE

Hereinafter, the present specification will be described in more detail.

One embodiment of the present specification provides an additive for an electrochemical device including a compound represented by the following Chemical Formula 1.

[Chemical Formula 1]

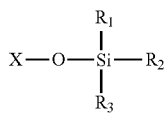

In Chemical Formula 1,

X is a substituted or unsubstituted monovalent aryl group, or a substituted or unsubstituted monovalent heteroaryl group, and $R_1$ to $R_3$ are the same as or different from each other, and each independently hydrogen or a monovalent organic group.

According to another embodiment of the present specification, the compound of Chemical Formula 1 may be represented by the following Chemical Formula 2.

[Chemical Formula 2]

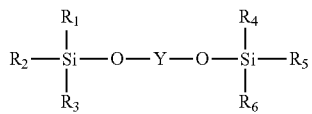

In Chemical Formula 2,

Y is a substituted or unsubstituted divalent aryl group, or a substituted or unsubstituted divalent heteroaryl group, and $R_1$ to $R_6$ are the same as or different from each other, and each independently hydrogen or a monovalent organic group.

According to another embodiment of the present specification, the compound of Chemical Formula 1 may be represented by the following Chemical Formula 3.

[Chemical Formula 3]

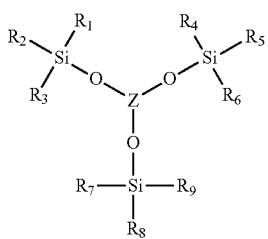

In Chemical Formula 3,

Z is a substituted or unsubstituted trivalent aryl group, or a substituted or unsubstituted trivalent heteroaryl group, and $R_1$ to $R_9$ are the same as or different from each other, and each independently hydrogen or a monovalent organic group.

According to another embodiment of the present specification, X of Chemical Formula 1 is a substituted or unsubstituted $C_6$ to $C_{30}$ aryl group.

According to another embodiment of the present specification, X of Chemical Formula 1 is a substituted or unsubstituted $C_6$ to $C_{14}$ aryl group.

According to another embodiment of the present specification, X of Chemical Formula 1 is a substituted or unsubstituted phenyl group, a substituted or unsubstituted biphenyl group, or a substituted or unsubstituted binaphthyl group.

According to another embodiment of the present specification, X of Chemical Formula 1 is a substituted or unsubstituted $C_6$ to $C_{30}$ heteroaryl group.

According to another embodiment of the present specification, X of Chemical Formula 1 is a substituted or unsubstituted $C_6$ to $C_{14}$ heteroaryl group.

According to another embodiment of the present specification, X of Chemical Formula 1 is a substituted or unsubstituted triazine group, or a substituted or unsubstituted pyrrole group.

According to another embodiment of the present specification, when X of Chemical Formula 1 is substituted, the substituent is a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, when X of Chemical Formula 1 is substituted, the substituent is a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and each independently hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, when X of Chemical Formula 1 is substituted, the substituent is a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, when X of Chemical Formula 1 is substituted, the substituent is a hydroxyl group or —OSiR$_a$R$_b$R$_c$, and herein, R$_a$, R$_b$ and R$_c$ are the same as or different from each other, and a C$_1$-C$_{20}$ alkyl group.

According to another embodiment of the present specification, when X of Chemical Formula 1 is substituted, the substituent is a hydroxyl group or —OSiR$_a$R$_b$R$_c$, and herein, R$_a$, R$_b$ and R$_c$ are the same as or different from each other, and a C$_1$-C$_6$ alkyl group.

According to another embodiment of the present specification, R$_1$ to R$_3$ of Chemical Formula 1 are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof.

According to another embodiment of the present specification, R$_1$ to R$_3$ of Chemical Formula 1 are the same as or different from each other, and each independently hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, R$_1$ to R$_3$ of Chemical Formula 1 are the same as or different from each other, and each independently a substituted or unsubstituted C$_1$ to C$_{20}$ alkyl group.

According to another embodiment of the present specification, R$_1$ to R$_3$ of Chemical Formula 1 are the same as or different from each other, and each independently a substituted or unsubstituted C$_1$ to C$_6$ alkyl group.

According to another embodiment of the present specification, R$_1$ to R$_3$ of Chemical Formula 1 are the same as or different from each other, and each independently a C$_1$ to C$_6$ alkyl group.

According to another embodiment of the present specification, R$_1$ to R$_3$ of Chemical Formula 1 are a methyl group.

According to another embodiment of the present specification, Y of Chemical Formula 2 is a substituted or unsubstituted C$_6$ to C$_{30}$ arylene group.

According to another embodiment of the present specification, Y of Chemical Formula 2 is a substituted or unsubstituted C$_6$ to C$_{14}$ arylene group.

According to another embodiment of the present specification, Y of Chemical Formula 2 is a substituted or unsubstituted phenylene group, a substituted or unsubstituted biphenyl group, or a substituted or unsubstituted binaphthyl group.

According to another embodiment of the present specification, Y of Chemical Formula 2 is a substituted or unsubstituted C$_6$ to C$_{30}$ heteroaryl group.

According to another embodiment of the present specification, Y of Chemical Formula 2 is a substituted or unsubstituted C$_6$ to C$_{14}$ heteroaryl group.

According to another embodiment of the present specification, Y of Chemical Formula 2 is a substituted or unsubstituted triazine group, or a substituted or unsubstituted pyrrole group.

According to another embodiment of the present specification, when Y of Chemical Formula 2 is substituted, the substituent is a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and herein, R$_a$ to R$_f$ are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and R$_g$ and R$_h$ are the same as or different from each other, and each independently a substituted or unsubstituted C$_1$-C$_{20}$ alkyl group, or a substituted or unsubstituted C$_6$-C$_{30}$ aryl group.

According to another embodiment of the present specification, when Y of Chemical Formula 2 is substituted, the substituent is a hydroxyl group, —OSiR$_a$R$_b$R$_c$, —SiR$_d$R$_e$R$_f$, —NR$_g$R$_h$, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and R$_g$ and R$_h$ are the same as or different from each other, and each independently a C$_1$-C$_{20}$ alkyl group, or a C$_6$-C$_{30}$ aryl group.

According to another embodiment of the present specification, when Y of Chemical Formula 2 is substituted, the substituent is a hydroxyl group or —OSiR$_a$R$_b$R$_c$, and herein, R$_a$, R$_b$ and R$_c$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, when Y of Chemical Formula 2 is substituted, the substituent is a hydroxyl group or —OSiR$_a$R$_b$R$_c$, and herein, R$_a$, R$_b$ and R$_c$ are the same as or different from each other, and a C$_1$-C$_{20}$ alkyl group.

According to another embodiment of the present specification, when Y of Chemical Formula 2 is substituted, the substituent is a hydroxyl group or —OSiR$_a$R$_b$R$_c$, and herein, R$_a$, R$_b$ and R$_c$ are the same as or different from each other, and a C$_1$-C$_6$ alkyl group.

According to another embodiment of the present specification, R$_1$ to R$_6$ of Chemical Formula 2 are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof.

According to another embodiment of the present specification, R$_1$ to R$_6$ of Chemical Formula 2 are the same as or different from each other, and each independently hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, R$_1$ to R$_6$ of Chemical Formula 2 are the same as or different from each other, and each independently a substituted or unsubstituted C$_1$ to C$_{20}$ alkyl group.

According to another embodiment of the present specification, R$_1$ to R$_6$ of Chemical Formula 2 are the same as or different from each other, and each independently a substituted or unsubstituted C$_1$ to C$_6$ alkyl group.

According to another embodiment of the present specification, R$_1$ to R$_6$ of Chemical Formula 2 are the same as or different from each other, and each independently a C$_1$ to C$_6$ alkyl group.

According to another embodiment of the present specification, R$_1$ to R$_6$ of Chemical Formula 2 are a methyl group.

According to another embodiment of the present specification, Z of Chemical Formula 3 is a substituted or unsubstituted C$_6$ to C$_{30}$ aryl group.

According to another embodiment of the present specification, Z of Chemical Formula 3 is a substituted or unsubstituted C$_6$ to C$_{14}$ aryl group.

According to another embodiment of the present specification, Z of Chemical Formula 3 is a substituted or unsubstituted phenyl group, a substituted or unsubstituted biphenyl group, or a substituted or unsubstituted binaphthyl group.

According to another embodiment of the present specification, Z of Chemical Formula 3 is a substituted or unsubstituted C$_6$ to C$_{30}$ heteroaryl group.

According to another embodiment of the present specification, Z of Chemical Formula 3 is a substituted or unsubstituted C$_6$ to C$_{14}$ heteroaryl group.

According to another embodiment of the present specification, Z of Chemical Formula 3 is a substituted or unsubstituted triazine group, or a substituted or unsubstituted pyrrole group.

According to another embodiment of the present specification, when Z of Chemical Formula 3 is substituted, the substituent is a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and herein, R$_a$ to R$_f$ are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and R$_g$ and R$_h$ are the same as or different from each other, and each independently a substituted or unsubstituted C$_1$-C$_{20}$ alkyl group, or a substituted or unsubstituted C$_6$-C$_{30}$ aryl group.

According to another embodiment of the present specification, when Z of Chemical Formula 3 is substituted, the substituent is a hydroxyl group, —OSiR$_a$R$_b$R$_c$, —SiR$_d$R$_e$R$_f$, —NR$_g$R$_h$, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and R$_g$ and R$_h$ are the same as or different from each other, and each independently a C$_1$-C$_{20}$ alkyl group, or a C$_6$-C$_{30}$ aryl group.

According to another embodiment of the present specification, R$_1$ to R$_9$ of Chemical Formula 3 are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof.

According to another embodiment of the present specification, R$_1$ to R$_9$ of Chemical Formula 3 are the same as or different from each other, and each independently hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, R$_1$ to R$_9$ of Chemical Formula 3 are the same as or different from each other, and each independently a substituted or unsubstituted C$_1$ to C$_{20}$ alkyl group.

According to another embodiment of the present specification, $R_1$ to $R_9$ of Chemical Formula 3 are the same as or different from each other, and each independently a substituted or unsubstituted $C_1$ to $C_6$ alkyl group.

According to another embodiment of the present specification, $R_1$ to $R_9$ of Chemical Formula 3 are the same as or different from each other, and each independently a $C_1$ to $C_6$ alkyl group.

According to another embodiment of the present specification, $R_1$ to $R_9$ of Chemical Formula 3 are a methyl group.

According to another embodiment of the present specification, the compound of Chemical Formula 1 is represented by the following Chemical Formula 4.

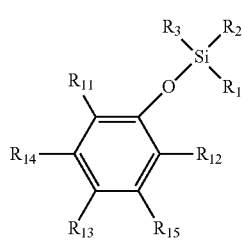

[Chemical Formula 4]

In Chemical Formula 4, $R_1$ to $R_3$ are the same as those defined in Chemical Formula 1, and $R_{11}$ to $R_{15}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{11}$ to $R_{15}$ of Chemical Formula 4 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, $R_{11}$ to $R_{15}$ of Chemical Formula 4 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, $R_{11}$ to $R_{15}$ of Chemical Formula 4 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, $R_{11}$ to $R_{15}$ of Chemical Formula 4 are hydrogen or a hydroxyl group.

According to another embodiment of the present specification, the compound of Chemical Formula 1 is represented by the following Chemical Formula 5.

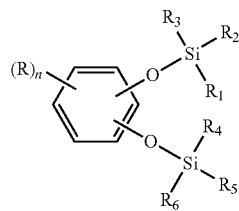

[Chemical Formula 5]

In Chemical Formula 5, $R_1$ to $R_6$ are the same as those defined in Chemical Formula 2, R is hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, and n is an integer of 1 to 4, and when n is 2 or more, Rs are the same as or different from each other.

According to another embodiment of the present specification, Rs of Chemical Formula 5 are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and R$_g$ and R$_h$ are the same as or different from each other, and each independently a $C_1$-$C_{20}$ alkyl group, or a $C_6$-$C_{30}$ aryl group.

According to another embodiment of the present specification, Rs of Chemical Formula 5 are the same as or different from each other, and each independently hydrogen, a hydroxyl group or —OSiR$_a$R$_b$R$_c$, and herein, R$_a$, R$_b$ and R$_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, Rs of Chemical Formula 5 are the same as or different from each other, and each independently hydrogen, a hydroxyl group or —OSiR$_a$R$_b$R$_c$, and herein, R$_a$, R$_b$ and R$_c$ are the same as or different from each other, and a $C_1$-$C_{20}$ alkyl group.

According to another embodiment of the present specification, R of Chemical Formula 5 is hydrogen.

According to another embodiment of the present specification, the compound of Chemical Formula 1 is represented by the following Chemical Formula 6.

[Chemical Formula 6]

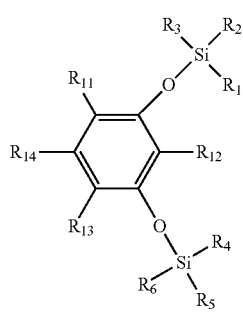

In Chemical Formula 6, $R_1$ to $R_6$ are the same as those defined in Chemical Formula 2, and $R_{11}$ to $R_{14}$ are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, R$_a$ to R$_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and R$_g$ and R$_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{11}$ to $R_{14}$ of Chemical Formula 6 are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and R$_g$ and R$_h$ are the same as or different from each other, and each independently a $C_1$-$C_{20}$ alkyl group, or a $C_6$-$C_{30}$ aryl group.

According to another embodiment of the present specification, $R_{11}$ to $R_{14}$ of Chemical Formula 6 are the same as or different from each other, and each independently hydrogen, a hydroxyl group or —OSiR$_a$R$_b$R$_c$, and herein, R$_a$, R$_b$ and R$_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, $R_{11}$ to $R_{14}$ of Chemical Formula 6 are the same as or different from each other, and each independently hydrogen, a hydroxyl group or —OSiR$_a$R$_b$R$_c$, and herein, R$_a$, R$_b$ and R$_c$ are the same as or different from each other, and a $C_1$-$C_{20}$ alkyl group.

According to another embodiment of the present specification, $R_{11}$ to $R_{14}$ of Chemical Formula 6 are hydrogen. According to another embodiment of the present specification, the compound of Chemical Formula 1 is represented by the following Chemical Formula 7.

[Chemical Formula 7]

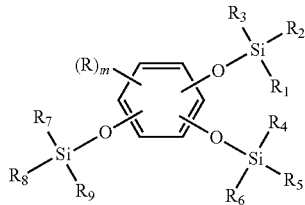

In Chemical Formula 7, $R_1$ to $R_9$ are the same as those defined in Chemical Formula 3, R is hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, and m is an integer of 1 to 3, and when m is 2 or more, Rs are the same as or different from each other.

According to another embodiment of the present specification, Rs of Chemical Formula 7 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, R of Chemical Formula 7 is hydrogen.

According to another embodiment of the present specification, the compound of Chemical Formula 1 is represented by the following Chemical Formula 8.

[Chemical Formula 8]

In Chemical Formula 8, $R_1$ to $R_9$ are the same as those defined in Chemical Formula 3, and $R_{11}$ to $R_{13}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{11}$ to $R_{13}$ of Chemical Formula 8 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, $R_{11}$ to $R_{13}$ of Chemical Formula 8 are hydrogen.

According to another embodiment of the present specification, the compound of Chemical Formula 1 is represented by the following Chemical Formula 9.

[Chemical Formula 9]

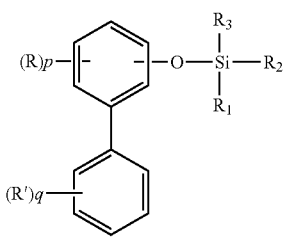

In Chemical Formula 9, $R_1$ to $R_3$ are the same as those defined in Chemical Formula 1, R and R' are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, p is an integer of 1 to 4, and when p is 2 or more, Rs are the same as or different from each other, and q is an integer of 1 to 5, and when q is 2 or more, R's are the same as or different from each other.

According to another embodiment of the present specification, R and R' of Chemical Formula 9 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, R and R' of Chemical Formula 9 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, R and R' of Chemical Formula 9 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, R and R' of Chemical Formula 9 are hydrogen.

According to another embodiment of the present specification, the compound of Chemical Formula 1 is represented by the following Chemical Formula 10.

[Chemical Formula 10]

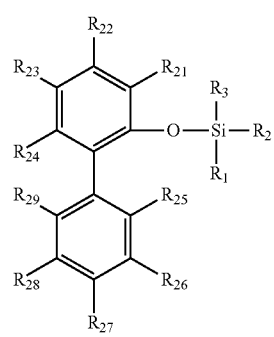

In Chemical Formula 10, $R_1$ to $R_3$ are the same as those defined in Chemical Formula 1, and $R_{21}$ to $R_{29}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{20}$ aryl group.

According to another embodiment of the present specification, $R_{21}$ to $R_{29}$ of Chemical Formula 10 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, $R_{21}$ to $R_{29}$ of Chemical Formula 10 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, $R_{21}$ to $R_{29}$ of Chemical Formula 10 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, $R_{21}$ to $R_{29}$ of Chemical Formula 10 are hydrogen or a hydroxyl group.

According to another embodiment of the present specification, the compound of Chemical Formula 1 is represented by the following Chemical Formula 11.

[Chemical Formula 11]

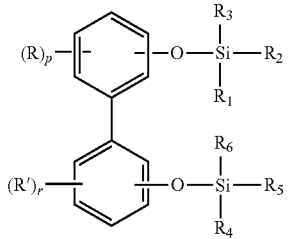

In Chemical Formula 11, $R_1$ to $R_6$ are the same as those defined in Chemical Formula 2, R and R' are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, p is an integer of 1 to 4, and when p is 2 or more, Rs are the same as or different from each other, and r is an integer of 1 to 4, and when r is 2 or more, R's are the same as or different from each other.

According to another embodiment of the present specification, R and R' of Chemical Formula 11 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, R and R' of Chemical Formula 11 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, R and R' of Chemical Formula 11 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, R and R' of Chemical Formula 11 are hydrogen.

According to another embodiment of the present specification, the compound of Chemical Formula 1 is represented by the following Chemical Formula 12.

[Chemical Formula 12]

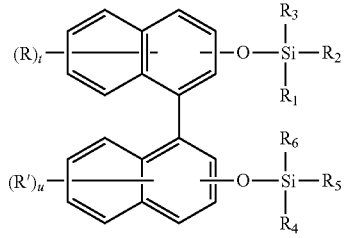

In Chemical Formula 12, $R_1$ to $R_6$ are the same as those defined in Chemical Formula 2, $R_{21}$ to $R_{28}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{21}$ to $R_{28}$ of Chemical Formula 12 are the same as or different from each other, and each independently hydrogen, a hydroxyl group, —$OSiR_aR_bR_c$, —$NR_dR_e$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_d$ and $R_e$ are the same as or different from each other, and each independently a $C_1$-$C_{20}$ alkyl group, or a $C_6$-$C_{30}$ aryl group.

According to another embodiment of the present specification, $R_{21}$ to $R_{28}$ of Chemical Formula 12 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, $R_{21}$ to $R_{28}$ of Chemical Formula 12 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, $R_{21}$ to $R_{28}$ of Chemical Formula 12 are hydrogen.

According to another embodiment of the present specification, the compound of Chemical Formula 1 is represented by the following Chemical Formula 13.

[Chemical Formula 13]

In Chemical Formula 13, $R_1$ to $R_6$ are the same as those defined in Chemical Formula 2, R and R' are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, t is an integer of 1 to 6, and when t is 2 or more, Rs are the same as or different from each other, and u is an integer of 1 to 6, and when u is 2 or more, R's are the same as or different from each other.

According to another embodiment of the present specification, the compound of Chemical Formula 1 is represented by the following Chemical Formula 14.

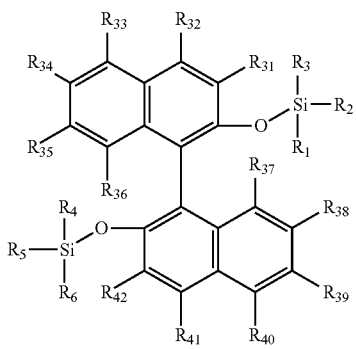

[Chemical Formula 14]

In Chemical Formula 14, $R_1$ to $R_6$ are the same as those defined in Chemical Formula 2, and $R_{31}$ to $R_{42}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{31}$ to $R_{42}$ of Chemical Formula 14 are hydrogen.

According to another embodiment of the present specification, the compound of Chemical Formula 1 is represented by the following Chemical Formula 15.

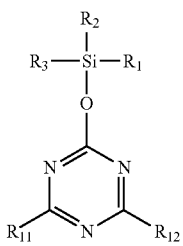

[Chemical Formula 15]

In Chemical Formula 15, $R_1$ to $R_3$ are the same as those defined in Chemical Formula 1, and $R_{11}$ and $R_{12}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{11}$ and $R_{12}$ of Chemical Formula 15 are the same as or different from each other, and each independently hydrogen, a hydroxyl group, —$OSiR_aR_bR_c$, —$SiR_dR_eR_f$ —NR$_g$R$_h$, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and R$_g$ and R$_h$ are the same as or different from each other, and each independently a C$_1$-C$_{20}$ alkyl group, or a C$_6$-C$_{30}$ aryl group.

According to another embodiment of the present specification, R$_{11}$ and R$_{12}$ of Chemical Formula 15 are the same as or different from each other, and each independently hydrogen, a hydroxyl group or —OSiR$_a$R$_b$R$_c$, and herein, R$_a$, R$_b$ and R$_c$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, R$_{11}$ and R$_{12}$ of Chemical Formula 15 are the same as or different from each other, and each independently hydrogen, a hydroxyl group or —OSiR$_a$R$_b$R$_c$, and herein, R$_a$, R$_b$ and R$_c$ are the same as or different from each other, and a C$_1$-C$_{20}$ alkyl group.

According to another embodiment of the present specification, R$_{11}$ and R$_{12}$ of Chemical Formula 15 are hydrogen or a hydroxyl group.

In another embodiment of the present specification, the compound of Chemical Formula 2 is represented by the following Chemical Formula 16.

[Chemical Formula 16]

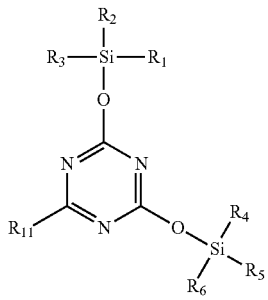

In Chemical Formula 16,

R$_1$ to R$_6$ are the same as those defined in Chemical Formula 2, and

R$_{11}$ is hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof or bonds to an adjacent group to form a ring, and herein, R$_a$ to R$_f$ are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and R$_g$ and R$_h$ are the same as or different from each other, and each independently a substituted or unsubstituted C$_1$-C$_{20}$ alkyl group, or a substituted or unsubstituted C$_6$-C$_{30}$ aryl group.

According to another embodiment of the present specification, R$_{11}$s of Chemical Formula 16 are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and herein, R$_a$ to R$_f$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof, and R$_g$ and R$_h$ are the same as or different from each other, and each independently a C$_1$-C$_{20}$ alkyl group, or a C$_6$-C$_{30}$ aryl group.

According to another embodiment of the present specification, R$_{11}$s of Chemical Formula 16 are the same as or different from each other, and each independently hydrogen, a hydroxyl group or —OSiR$_a$R$_b$R$_c$, and herein, R$_a$, R$_b$ and R$_c$ are the same as or different from each other, and hydrogen, a hydroxyl group, an ester group, a carbonate group, a carbonyl group, a thio group, a C$_1$-C$_{20}$ alkyl group, a C$_1$-C$_{20}$ alkoxy group, a C$_2$-C$_{20}$ alkenyl group, a C$_2$-C$_{20}$ alkynyl group, a C$_2$-C$_{20}$ alkylene oxide group, a C$_3$-C$_{30}$ cycloalkyl group, a C$_6$-C$_{30}$ aryl group, a C$_6$-C$_{30}$ aryloxy group, a C$_2$-C$_{30}$ heteroaryl group, or a combination thereof.

According to another embodiment of the present specification, R$_{11}$s of Chemical Formula 16 are the same as or different from each other, and each independently hydrogen, a hydroxyl group or —OSiR$_a$R$_b$R$_c$, and herein, R$_a$, R$_b$ and R$_c$ are the same as or different from each other, and a C$_1$-C$_{20}$ alkyl group.

According to another embodiment of the present specification, R$_{11}$ of Chemical Formula 16 is a hydroxyl group.

In one embodiment of the present specification, the compound of Chemical Formula 3 is represented by the following Chemical Formula 17.

[Chemical Formula 17]

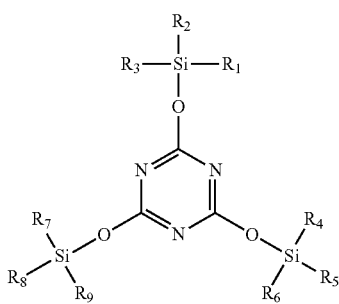

In Chemical Formula 17,
$R_1$ to $R_9$ are the same as those defined in Chemical Formula 3.

In one embodiment of the present specification, the compound of Chemical Formula 1 is represented by the following Chemical Formula 18.

[Chemical Formula 18]

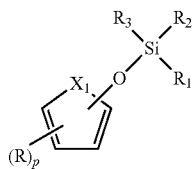

In Chemical Formula 18,
$R_1$ to $R_3$ are the same as those defined in Chemical Formula 1, $X_1$ is O, S or NH, R is hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, and p is an integer of 1 to 3, and when p is 2 or more, Rs are the same as or different from each other.

In one embodiment of the present specification, the compound of Chemical Formula 1 is represented by the following Chemical Formula 19.

[Chemical Formula 19]

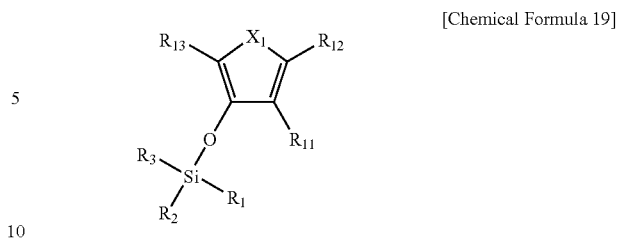

In Chemical Formula 19,
$R_1$ to $R_3$ are the same as those defined in Chemical Formula 1, $X_1$ is O, S or NH, and $R_{11}$ to $R_{13}$ are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

According to another embodiment of the present specification, $R_{11}$ to $R_{13}$ of Chemical Formula 19 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, $R_{11}$ to $R_{13}$ of Chemical Formula 19 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, $R_{11}$ to $R_{13}$ of Chemical Formula 19 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, $R_{11}$ to $R_{13}$ of Chemical Formula 19 are hydrogen or a hydroxyl group.

In one embodiment of the present specification, $R_{12}$ of Chemical Formula 19 is a hydroxyl group.

In one embodiment of the present specification, $R_{11}$ and $R_{13}$ of Chemical Formula 19 are hydrogen.

In one embodiment of the present specification, $R_{12}$ of Chemical Formula 19 is a hydroxyl group, and $R_{11}$ and $R_{13}$ are hydrogen.

In one embodiment of the present specification, $X_1$ of Chemical Formula 19 is NH.

In another embodiment of the present specification, the compound of Chemical Formula 2 is represented by the following Chemical Formula 20.

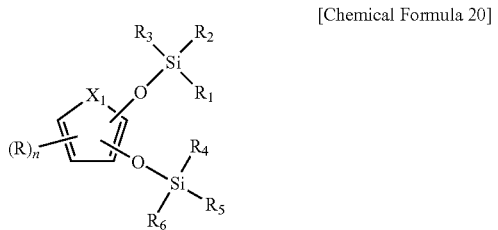

[Chemical Formula 20]

In Chemical Formula 20, $R_1$ to $R_6$ are the same as those defined in Chemical Formula 2, $X_1$ is O, S or NH, R is hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, and n is 1 or 2, and when n is 2, Rs are the same as or different from each other.

According to another embodiment of the present specification, Rs of Chemical Formula 20 are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, Rs of Chemical Formula 20 are the same as or different from each other, and each independently hydrogen, a hydroxyl group or —$OSiR_aR_bR_c$, and herein, $R_a$, $R_b$ and $R_c$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

According to another embodiment of the present specification, Rs of Chemical Formula 20 are the same as or different from each other, and each independently hydrogen, a hydroxyl group or —$OSiR_aR_bR_c$, and herein, $R_a$, $R_b$ and $R_c$ are the same as or different from each other, and a $C_1$-$C_{20}$ alkyl group.

According to another embodiment of the present specification, R of Chemical Formula 20 is hydrogen.

According to one embodiment of the present specification, the compound of Chemical Formula 3 is represented by the following Chemical Formula 21.

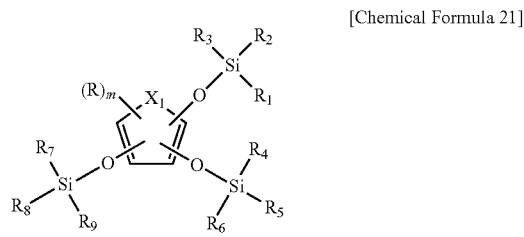

[Chemical Formula 21]

In Chemical Formula 21, $R_1$ to $R_9$ are the same as those defined in Chemical Formula 3, $X_1$ is O, S or NH, R is hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group, and m is 1.

According to another embodiment of the present specification, Rs of Chemical Formula 21 are the same as or different from each other, and each independently hydrogen, a hydroxyl group, —OSi$R_aR_bR_c$, —Si$R_dR_eR_f$, —N$R_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

According to another embodiment of the present specification, R of Chemical Formula 21 is hydrogen.

According to another embodiment of the present specification, $X_1$ of Chemical Formula 21 is NH.

The additive for an electrochemical device may be added to an electrolyte, or may be formed as a membrane formed by an oxidative polymerization reaction of a material produced by the compound of any one of Chemical Formulae 1 to 21 collecting an acid component such as HF on a portion of the surface or on the surface of an electrode. The membrane provided on a portion of the surface or on the surface of the electrode may be formed on a portion or the whole of the surface of the electrode by adding the additive for an electrochemical device described above to an electrolyte when preparing a battery, or may be formed by directly applying the additive for an electrochemical device on an electrode. The additive for an electrochemical device prevents battery performance decline caused by an acid component such as HF, reduces a voltage drop even when stored at high temperatures by improving a high-temperature cycle property, and enhances high-temperature storage efficiency. In addition, the additive for an electrochemical device may simultaneously improve various properties such as capacity, a lifespan, an output and a high-temperature property through forming a protective membrane on the electrode surface. According to one example, the additive for an electrochemical device according to the embodiments described above is capable of being used at a high voltage of 4.4 V.

It is to be noted that the protective film provided on the surface of the electrode according to the embodiments of the present specification is not a compound represented by any one of Chemical Formulae 1 to 21 itself, and includes a product formed by an oxidative polymerization reaction of a material produced by the compound collecting an acid component such as HF. The protective film including such a product not only efficiently performs a role of a protective film, but also is capable of naturally forming a membrane on the surface of an electrode as necessary by being used as an electrolyte additive in a battery without a separate membrane forming process, when compared to a case in which a layer formed with the compound represented by any one of Chemical Formulae 1 to 21 itself is formed on one surface of an electrode, and therefore, has an advantage in terms of a process.

Examples of the substituents are described below, however, the substituents are not limited thereto.

In the present specification, the term "substituted or unsubstituted" means being substituted with one or more substituents selected from the group consisting of a hydroxyl group, —OSi$R_aR_bR_c$, —Si$R_dR_eR_f$, —N$R_gR_h$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group or a combination thereof, or having no substituents. Herein, $R_a$ to $R_f$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and $R_g$ and $R_h$ are the same as or different from each other, and each independently a $C_1$-$C_{20}$ alkyl group, or a $C_6$-$C_{30}$ aryl group.

In the present specification, the alkyl group may be linear or branched, and the number of carbon atoms is not particularly limited, but is preferably 1 to 20. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably 2 to 20. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the aryl group may be a monocyclic aryl group or a multicyclic aryl group. The number of carbon atoms of the aryl group is not particularly limited, but is preferably 6 to 30. Specific examples of the aryl group may include a phenyl group, a biphenyl group, a terphenyl group, a naphthyl group, a binaphthyl group, an anthracenyl group, a phenanthryl group, a pyrenyl group, a perylenyl group, a crycenyl group, a fluorenyl group and the like, but are not limited thereto.

In the present specification, the heteroaryl group is a cyclic group including one or more of O, N and S as a heteroatom, and although not particularly limited, the number of carbon atoms is preferably 2 to 30. Examples of the heteroaryl group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the descriptions on the alkyl group made above may apply to alkylene in the alkylene oxide group except that the alkylene is a divalent group.

In the present specification, the descriptions on the aryl group made above may apply to aryl in the aryloxy group.

In the present specification, the ester group may be represented by —COOR$_f$; and R$_f$ means being substituted with one or more substituents selected from the group consisting of a hydroxyl group, —OSiR$_g$R$_h$R$_i$, —NR$_j$R$_k$, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, or having no substituents. Herein, R$_g$, R$_h$ and R$_i$ are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and R$_j$ and R$_k$ are the same as or different from each other, and each independently a $C_1$-$C_{20}$ alkyl group, or a $C_6$-$C_{30}$ aryl group.

In the present specification, the carbonate group may be represented by —CO$_3$R$_m$; and R$_m$ has the same definition as R$_f$ described above.

In the present specification, the carbonyl group may be represented by —COR$_n$; and R$_n$ has the same definition as R$_f$ described above.

In the present specification, the "combination" of substituents means a structure in which two or more substituents bond.

The compound represented by any one of Chemical Formulae 1 to 21 according to the embodiments described above forms a membrane or film from an oxidative polymerization reaction after collecting HF.

According to one embodiment of the present specification, the electrolyte includes an additive for an electrochemical device including the compound represented by any one of Chemical Formulae 1 to 21 according to the embodiments described above.

According to one embodiment of the present specification, the content of the compound represented by any one of Chemical Formulae 1 to 21 according to the embodiments described above in the electrolyte is from 0.01% by weight to 5% by weight. When the compound represented by any one of Chemical Formulae 1 to 21 is included in less than 0.01% by total weight of the electrolyte, a target effect of maintaining a lifespan may be insignificant, and when included in 5% by weight or less, performance decline of an electrochemical device due to the additive may be prevented.

According to another embodiment of the present specification, the content of the compound represented by any one of Chemical Formulae 1 to 21 according to the embodiments described above in the electrolyte is from 0.01% by weight to 2% by weight.

According to another embodiment of the present specification, the content of the compound represented by any one of Chemical Formulae 1 to 21 according to the embodiments described above in the electrolyte is from 0.05% by weight to 1% by weight.

According to one embodiment of the present specification, the electrolyte may further include an electrolyte salt and an electrolyte solvent.

According to one embodiment of the present specification, the electrolyte salt may be a salt including a lithium cation, an anion such as $PF_6^-$, $BF_4^-$, $Cl^-$, $Br^-$, $I^-$, $ClO_4^-$, $AsF_6^-$, $SO_3CF_3^-$, $N(SO_2CF_3)_2^-$ and $N(SO_2F)_2^-$, or an ion formed with a combination of one or more of these.

According to one embodiment of the present specification, the electrolyte solvent may be an organic solvent, and specifically cyclic carbonate, linear carbonate, cyclic ester, linear ester and a combination thereof. More specifically, nonlimiting examples of the electrolyte solvent may include propylene carbonate (PC), ethylene carbonate (EC), diethyl carbonate (DEC), dimethyl carbonate (DMC), ethylmethyl carbonate (EMC), dipropyl carbonate (DPC), dimethyl sulfoxide, acetonitrile, dimethoxyethane, diethoxyethane, tetrahydrofuran (THF), N-methyl-2-pyrrolidone (NMP), gamma butyrolactone (GBL), fluoroethylene carbonate (FEC), methyl formate, ethyl formate, propyl formate, methyl acetate, ethyl acetate, propyl acetate, butyl acetate and the like. The organic solvent may be used either alone or as a combination of two or more types. When two or more types are mixed and used, the mixing ratio may be properly adjusted depending on a target performance of a lithium secondary battery, and this may be widely understood to those skilled in the art. In addition, halogen derivatives of the organic solvent may also be used.

According to one embodiment of the present specification, the electrolyte may be a non-aqueous electrolyte.

According to one embodiment of the present specification, the electrolyte may be for an electrochemical device. Specifically, the electrolyte may be for a lithium secondary battery.

One embodiment of the present specification provides an electrode provided with a membrane formed by an oxidative polymerization reaction of a material produced by the compound represented by any one of Chemical Formulae 1 to 21 described above collecting an acid component such as HF on a portion or the whole of a surface. The thickness of the membrane may be adjusted as necessary.

According to one embodiment of the present specification, the polymer included in the membrane formed by an oxidative polymerization reaction of a material produced by the compound represented by any one of Chemical Formulae 1 to 21 described above collecting an acid component such as HF may have a repeating unit of the following Chemical Formula 22 or 23.

[Chemical Formula 22]

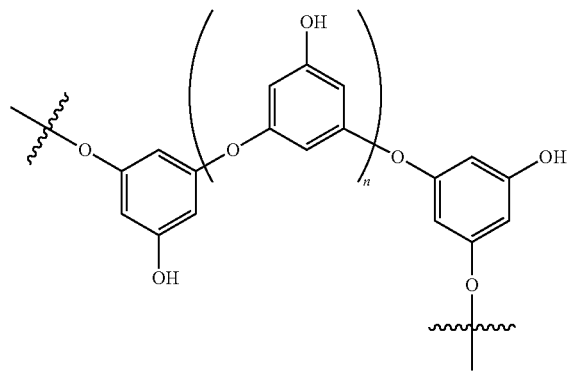

[Chemical Formula 23]

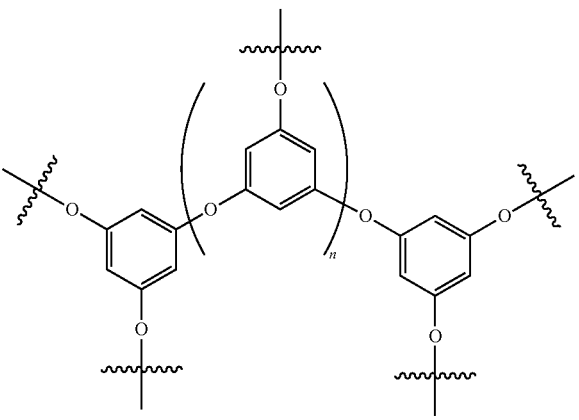

Chemical Formula 22 or 23 may have an additional substituent. Examples of the additional substituent capable of substituting Chemical Formula 15 or 16 include a hydroxyl group, —OSiRR'R", —SiRR'R", —NRR', an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof, and herein, R, R' and R" are the same as or different from each other, and hydrogen, a hydroxyl group, an ester group, a carbonate group, a carbonyl group, a thio group, a $C_1$-$C_{20}$ alkyl group, a $C_1$-$C_{20}$ alkoxy group, a $C_2$-$C_{20}$ alkenyl group, a $C_2$-$C_{20}$ alkynyl group, a $C_2$-$C_{20}$ alkylene oxide group, a $C_3$-$C_{30}$ cycloalkyl group, a $C_6$-$C_{30}$ aryl group, a $C_6$-$C_{30}$ aryloxy group, a $C_2$-$C_{30}$ heteroaryl group, or a combination thereof.

However, the polymer included in the membrane is not limited to those including only the repeating unit of Chemical Formula 22 or 23, and is not particularly limited as long as the polymer is formed from an oxidative polymerization reaction of a material produced by the compound represented by any one of Chemical Formulae 1 to 21 described above collecting an acid component such as HF.

According to one embodiment of the present specification, the electrode may be an anode, a cathode, or an anode and a cathode. Specifically, the electrode may be an anode.

One embodiment of the present specification relates to a secondary battery including an anode, a cathode, a separation membrane and an electrolyte, wherein the electrolyte includes the additive for an electrochemical device described above.

One embodiment of the present specification relates to a secondary battery including an anode, a cathode, a separation membrane and an electrolyte, wherein the electrolyte includes the additive for an electrochemical device described above, and at least one of the anode and the cathode is an electrode provided with a membrane formed by an oxidative polymerization reaction of a material produced by the compound represented by any one of Chemical Formulae 1 to 21 described above collecting an acid component such as HF on a portion or the whole of a surface.

One embodiment of the present specification relates to an electrochemical device including an anode, a cathode, a separation membrane and an electrolyte, wherein at least one of the anode and the cathode is an electrode provided with a membrane formed by an oxidative polymerization reaction of a material produced by the compound represented by any one of Chemical Formulae 1 to 21 described above collecting an acid component such as HF on a portion or the whole of a surface.

According to one embodiment of the present specification, the anode includes an anode active material including a transition material, and includes a membrane formed by an oxidative polymerization reaction of a material produced by the compound represented by any one of Chemical Formulae 1 to 21 collecting an acid component such as HF on a portion or the whole of a surface of the anode.

According to one embodiment of the present specification, the electrochemical device may be a secondary battery, for example, a lithium secondary battery.

According to one embodiment of the present specification, the cathode may be prepared using materials and methods known in the art, and for example, may be prepared by mixing and stirring a cathode active material, a binder, a solvent, a conductor and/or a dispersing agent to prepare slurry, then coating the slurry on a current collector of a metal material, and then extruding and drying the result.

According to one embodiment of the present specification, the cathode active material may use common cathode active materials capable of being used in a cathode of an existing secondary battery. Nonlimiting examples of the cathode active material may include a material occluding lithium such as a lithium metal or lithium metal alloys, coke, activated carbon, graphite, graphitized carbon, carbon nanotubes, graphine and/or other carbons. As the cathode current collector, foil by copper, nickel and the like, a combination of alloys thereof, and the like, may be used.

According to one embodiment of the present specification, the anode may be prepared in the form of coating an anode active material on an anode current collector according to general methods. The anode active material may use common materials used as an anode active material of a secondary battery without limits, and examples thereof may include $LiCoO_2$, $LiMnO_2$, $LiMn_2O_4$, $Li(Ni_aCo_bMn_c)O_2$ (a, b, c each are a number from 0 to 1, and a+b+c=1), $LiFePO_4$ or a mixture of any one or more of these. As the anode current collector, foil by aluminum, nickel and the like, a combination of alloys of one or more of these, and the like, may be included.

According to one embodiment of the present specification, the separation membrane is not particularly limited, and may have a porous membrane form. Specifically, the separation membrane may include those formed as polyethylene, polypropylene, and other polyolefin-based membranes or multilayer membranes thereof. Alternatively, those using ceramic coating on the separation membrane may be included.

The secondary battery according to one embodiment of the present specification may be manufactured using common methods known in the art, and may be manufactured by injecting an electrolyte to a cylindrical, a rectangular or a pouch-type case assembled including the cathode, the anode and the separation membrane.

MODE FOR DISCLOSURE

Hereinafter, the present specification will be described in detail with reference to examples. However, examples according to the present specification may be modified to various other forms, and the scope of the present specification is not interpreted to be limited to the examples described below. The examples of the present specification are provided in order to more completely describe the present specification for those having average knowledge in the art.

Examples 1 to 8

An electrolyte was prepared by adding 0.5% by weight of the compound of the following Table 1 to a 1 M $LiPF_6$ solution of ethylene carbonate and ethylmethyl carbonate mixed in a 1:2 volume ratio.

In order to prepare a cathode, 90% by weight of graphite carbon and 10% by weight of polyvinylidene difluoride (PVDF) were placed in N-methyl-2-pyrrolidone (NMP) and mixed for 2 hours in a mixer, then the result was coated on copper foil, and dried at 150° C. In order to prepare an anode, 90% by weight of $LiCoO_2$, 3% by weight of PVDF, and 7% by weight of carbon black were mixed for 2 hours as NMP slurry, then the result was coated on aluminum foil, and dried at 150° C. A polyolefin-based separation membrane was placed between the prepared cathode and the anode, and a cylindrical secondary battery was manufactured by injecting the electrolyte thereto.

Comparative Example 1

Comparative Example 1 was carried out in the same manner as in Examples except that the compound of the following Table 1 was used.

Test Example

Tests as follows were carried out for each secondary battery manufactured in Examples 1 to 8 and Comparative Example 1. Changes in the battery discharge capacity were measured for each battery by repeating charging and discharging with a current of 0.5 C at 23° C. and 45° C. in a range of 4.4 V and 3 V. In order to identify an anode protection effect, the battery was charged up to 4.4 V instead of 4.2 V, and discharged at a relatively fast controlling rate (C-rate) of 1.0 C instead of 0.5 C. Discharge capacity retention rates after 200 charging and discharging cycles with respect to initial discharge capacity are shown in the following Table 1.

TABLE 1

|  | Additive | Discharge Capacity Retention Rate (%) 23° C. | Discharge Capacity Retention Rate (%) 45° C. | Battery Voltage (V) after Storing for 50 Days at 60° C. | Battery Voltage Retention Rate (%) after Storing for 50 Days at 60° C. |
|---|---|---|---|---|---|
| Example 1 | 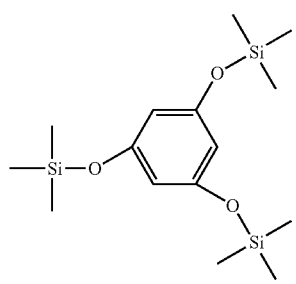 | 88.8 | 85.4 | 4.32 | 98.2 |

TABLE 1-continued

| Additive | Discharge Capacity Retention Rate (%) 23° C. | Discharge Capacity Retention Rate (%) 45° C. | Battery Voltage (V) after Storing for 50 Days at 60° C. | Battery Voltage Retention Rate (%) after Storing for 50 Days at 60° C. |
|---|---|---|---|---|
| Example 2 [3,5-bis(trimethylsilyloxy)phenol] | 86.0 | 83.2 | 4.24 | 96.4 |
| Example 3 [1,3-bis(trimethylsilyloxy)benzene] | 90.2 | 86.6 | 4.34 | 98.6 |
| Example 4 [2,2'-bis(trimethylsilyloxy)biphenyl] | 86.4 | 82.8 | 4.20 | 95.5 |
| Example 5 [2'-(trimethylsilyloxy)-2-hydroxybiphenyl] | 85.2 | 82 | 4.14 | 94.1 |
| Example 6 [2,2'-bis(trimethylsilyloxy)-1,1'-binaphthyl] | 86.8 | 82.8 | 4.22 | 95.9 |
| Example 7 [2,4-bis(trimethylsilyloxy)-6-hydroxy-1,3,5-triazine] | 85.8 | 82.2 | 4.15 | 94.3 |

TABLE 1-continued

| Additive | Discharge Capacity Retention Rate (%) 23° C. | Discharge Capacity Retention Rate (%) 45° C. | Battery Voltage (V) after Storing for 50 Days at 60° C. | Battery Voltage Retention Rate (%) after Storing for 50 Days at 60° C. |
|---|---|---|---|---|
| Example 8 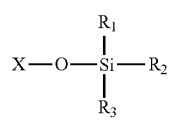 | 86.2 | 82.8 | 4.20 | 95.5 |
| Comparative Example 1 — No Additives | 72.8 | 56.2 | 3.54 | 80.0 |

As shown in Table 1, discharge capacity retention rates and high-temperature storage efficiency were shown to be excellent in Examples compared to Comparative Example. Accordingly, it was identified that additives according to the embodiments of the present specification were capable of improving capacity retention of an electrochemical device.

In Examples, the discharge capacity retention rate (%), the battery voltage (V) after storing for 50 days at 60° C. and the battery voltage retention rate (%) were measured as follows.

[Method of Measuring Discharge Capacity Retention Rate]

The manufactured lithium secondary batteries were charged up to 4.4 V at a 0.5 C-rate, and then discharged to 3.0 V at a 1.0 C-rate, and changes in the capacity were observed.

The battery voltage (V) after storing for 50 days at 60° C. means a value measuring OCV for 50 days at 60° C. after charging the battery up to 4.4 V at a 0.5 C-rate.

The battery voltage retention rate (%) means a ratio of the voltage after storing for 50 days at 60° C. with respect to the voltage (4.4 V) prior to high-temperature storage at 60° C.

The invention claimed is:

1. A secondary battery comprising:
an anode; a cathode; a separation membrane; and
an electrolyte comprising: an additive for an electrochemical device comprising a compound represented by the following Chemical Formula 1:

[Chemical Formula 1]

$$X-O-\underset{\underset{R_3}{|}}{\overset{\overset{R_1}{|}}{Si}}-R_2$$

wherein, in Chemical Formula 1;
X is a substituted or unsubstituted monovalent aryl group, or a substituted or unsubstituted monovalent heteroaryl group; and
$R_1$ to $R_3$ are the same as or different from each other, and each independently hydrogen or a monovalent organic group; and
wherein at least one of the anode and the cathode is provided with a membrane formed by an oxidative polymerization reaction of a material produced by the compound represented by Chemical Formula 1 collecting an acid component on a portion or the whole of a surface.

2. The secondary battery of claim 1, wherein the compound of Chemical Formula 1 represented by the following Chemical Formula 2:

[Chemical Formula 2]

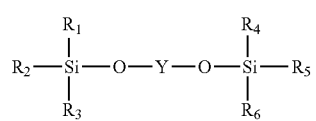

wherein, in Chemical Formula 2,
Y is a substituted or unsubstituted divalent aryl group, or a substituted or unsubstituted divalent heteroaryl group; and
$R_1$ to $R_6$ are the same as or different from each other, and each independently hydrogen or a monovalent organic group.

3. The secondary battery of claim 1, wherein the compound of Chemical Formula 1 is represented by the following Chemical Formula 3:

[Chemical Formula 3]

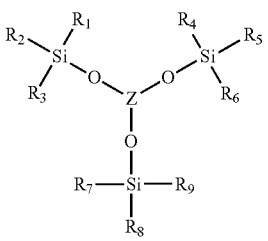

wherein, in Chemical Formula 3,
Z is a substituted or unsubstituted trivalent aryl group, or a substituted or unsubstituted trivalent heteroaryl group; and
$R_1$ to $R_9$ are the same as or different from each other, and each independently hydrogen or a monovalent organic group.

4. The secondary battery of claim 1, wherein the compound of Chemical Formula 1 is represented by the following Chemical Formula 4:

[Chemical Formula 4]

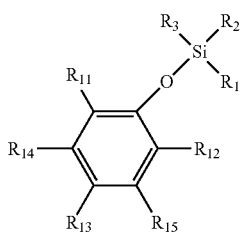

wherein, in Chemical Formula 4, $R_1$ to $R_3$ are the same as those defined in Chemical Formula 1; and $R_{11}$ to $R_{15}$ are the same as or different from each other, and each independently hydrogen, a hydroxyl group, $-OSiR_aR_bR_c$, $-SiR_dR_eR_f$, $-NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group.

5. The secondary battery of claim 2, wherein the compound of Chemical Formula 2 is represented by the following Chemical Formula 5:

[Chemical Formula 5]

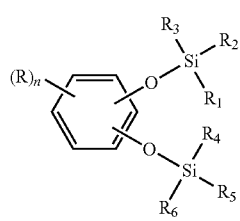

wherein, in Chemical Formula 5, $R_1$ to $R_6$ are the same as those defined in Chemical Formula 2;

R is hydrogen, a hydroxyl group, $-OSiR_aR_bR_c$, $-SiR_dR_eR_f$, $-NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group; and n is an integer of 1 to 4, and when n is 2 or more, Rs are the same as or different from each other.

6. The secondary battery of claim 3, wherein the compound of Chemical Formula 3 is represented by the following Chemical Formula 7:

[Chemical Formula 7]

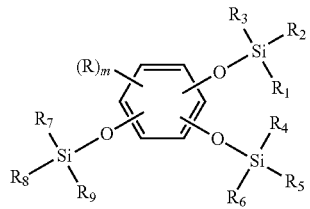

wherein, in Chemical Formula 7, $R_1$ to $R_9$ are the same as those defined in Chemical Formula 3;

R is hydrogen, a hydroxyl group, $-OSiR_aR_bR_c$, $-SiR_dR_eR_f$, $-NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bonds to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group; and m is an integer of 1 to 3, and when m is 2 or more, Rs are the same as or different from each other.

7. The secondary battery of claim 1, wherein the compound of Chemical Formula 1 is represented by the following Chemical Formula 9:

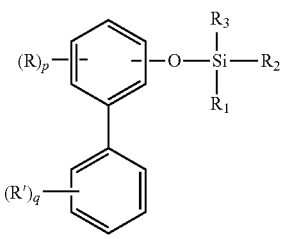

[Chemical Formula 9]

wherein, in Chemical Formula 9, $R_1$ to $R_3$ are the same as those defined in Chemical Formula 1;

R and R' are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group;

p is an integer of 1 to 4, and when p is 2 or more, Rs are the same as or different from each other; and q is an integer of 1 to 5, and when q is 2 or more, R's are the same as or different from each other.

8. The secondary battery of claim 2, wherein the compound of Chemical Formula 2 is represented by the following Chemical Formula 11:

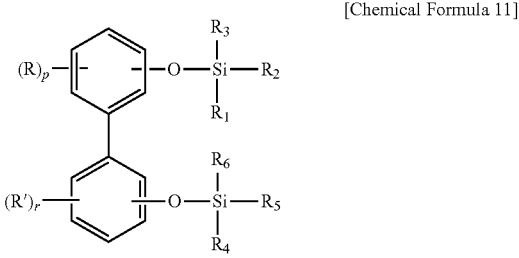

[Chemical Formula 11]

wherein, in Chemical Formula 11, $R_1$ to $R_6$ are the same as those defined in Chemical Formula 2;

R and R' are the same as or different from each other, and each independently hydrogen, a hydroxyl group, —$OSiR_aR_bR_c$, —$SiR_dR_eR_f$, —$NR_gR_h$, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof or bond to an adjacent group to form a ring, and herein, $R_a$ to $R_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group;

p is an integer of 1 to 4, and when p is 2 or more, Rs are the same as or different from each other; and r is an integer of 1 to 4, and when r is 2 or more, R's are the same as or different from each other.

9. The secondary battery of claim 2, wherein the compound of Chemical Formula 2 is represented by the following Chemical Formula 13:

[Chemical Formula 13]

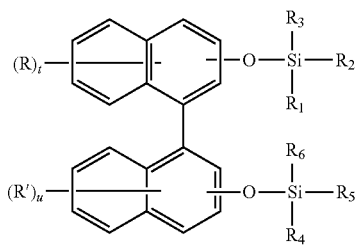

wherein, in Chemical Formula 13,
R$_1$ to R$_6$ are the same as those defined in Chemical Formula 2;
R and R' are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof or bond to an adjacent group to form a ring, and herein, R$_a$ to R$_f$ are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and R$_g$ and R$_h$ are the same as or different from each other, and each independently a substituted or unsubstituted C$_1$-C$_{20}$ alkyl group, or a substituted or unsubstituted C$_6$-C$_{30}$ aryl group;
t is an integer of 1 to 6, and when t is 2 or more, Rs are the same as or different from each other; and
u is an integer of 1 to 6, and when u is 2 or more, R's are the same as or different from each other.

10. The secondary battery of claim 1, wherein the compound of Chemical Formula 1 is represented by the following Chemical Formula 15:

[Chemical Formula 15]

wherein, in Chemical Formula
R$_1$ to R$_3$ are the same as those defined in Chemical Formula 1; and
R$_{11}$ and R$_{12}$ are the same as or different from each other, and each independently hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof or bond to an adjacent group to form a ring, and herein, R$_a$ to R$_f$ are the same as or different from each other, and each independently hydrogen, a hydroxyl group, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof, and R$_g$ and R$_h$ are the same as or different from each other, and each independently a substituted or unsubstituted C$_1$-C$_{20}$ alkyl group, or a substituted or unsubstituted C$_6$-C$_{30}$ aryl group.

11. The secondary battery of claim 1, wherein the compound of Chemical Formula 1 is represented by the following Chemical Formula 18:

[Chemical Formula 18]

wherein, in Chemical Formula 18,
R$_1$ to R$_3$ are the same as those defined in Chemical Formula 1;
X$_1$ is O, S or NH;
Rs are the same as or different from each other, and hydrogen, a hydroxyl group, —OSiR$_a$R$_b$R$_c$, —SiR$_d$R$_e$R$_f$, —NR$_g$R$_h$, an ester group, a carbonate group, a carbonyl group, a thio group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_2$-C$_{20}$ alkylene oxide group, a substituted or unsubstituted C$_3$-C$_{30}$ cycloalkyl group, a substituted or unsubstituted C$_6$-C$_{30}$ aryl group, a substituted or unsubstituted C$_6$-C$_{30}$ aryloxy group, a substituted or unsubstituted C$_2$-C$_{30}$ heteroaryl group, or a combination thereof or bond to an adjacent group to form a ring, and herein, R$_a$ to R$_f$ are the same as or different from each other, and each independently hydrogen, a hydroxyl group, an ester group, a carbonate group, a carbonyl group, a thio group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, or a combination thereof, and $R_g$ and $R_h$ are the same as or different from each other, and each independently a substituted or unsubstituted $C_1$-$C_{20}$ alkyl group, or a substituted or unsubstituted $C_6$-$C_{30}$ aryl group; and p is an integer of 1 to 3, and when p is 2 or more, Rs are the same as or different from each other.

12. The secondary battery of claim 1, further comprising an electrolyte salt and an electrolyte solvent.

13. The secondary battery of claim 1 comprising the compound of Chemical Formula 1 in 0.01 wt % or more and 5 wt % or less by total weight of the electrolyte.

14. The secondary battery of claim 1, wherein the electrolyte is a non-aqueous electrolyte.

* * * * *